United States Patent [19]

Gust, Jr. et al.

[11] Patent Number: 5,286,474
[45] Date of Patent: Feb. 15, 1994

[54] USE OF CAROTENOPORPHYRINS AS TUMOR LOCALIZING AGENTS FOR DIAGNOSIS

[75] Inventors: John D. Gust, Jr., Tempe; Ana L. Moore; Thomas A. Moore, both of Scottsdale, all of Ariz.; Giulio Jori, Padova; Elena Reddi, Rovigo, both of Italy

[73] Assignee: Arizona Board of Regents, a body corporate, acting for and on behalf the Arizona State University, Tempe, Ariz.

[21] Appl. No.: 966,136

[22] Filed: Oct. 22, 1992

[51] Int. Cl.$^5$ .................. A61B 5/00; A61K 31/555; A61K 31/40; C07B 47/00
[52] U.S. Cl. .................. 424/7.1; 540/145; 514/184; 514/410; 436/172; 436/800
[58] Field of Search .................. 424/7.1, 9; 540/145; 514/184, 410; 436/800, 172

[56] References Cited

U.S. PATENT DOCUMENTS

| | | | |
|---|---|---|---|
| 4,806,488 | 2/1989 | Berger et al. | 436/536 |
| 5,015,463 | 5/1991 | Dougherty et al. | 424/7.1 |
| 5,149,708 | 9/1992 | Dolphin et al. | 514/410 |

OTHER PUBLICATIONS

Land, E. J. et al. *J. Phys. Chem.* 91(18):4831–4835 (1987).

*Primary Examiner*—Gary Hollinden
*Attorney, Agent, or Firm*—Richard R. Mybeck

[57] ABSTRACT

A process of tumor identification comprising administering a carotenoporphyrin to a tumor-bearing mammalian host and irradiating the mammalian host with light whereupon the carotenoporphyrin, which has been preferentially taken up by the tumor tissue, fluoresces and permits precise identification of the location, size and shape of the tumor tissue. An improved process of synthesizing carotenoporphyrins 1–5 is also provided.

9 Claims, No Drawings

USE OF CAROTENOPORPHYRINS AS TUMOR LOCALIZING AGENTS FOR DIAGNOSIS

BACKGROUND OF THE INVENTION

1. Field of the Invention

The present invention relates to a method of diagnosing mammalian tumors and more particularly to a photoidentification method of diagnosing tumor tissue using a synthetic carotenoporphyrin which consists of a carotenoid polyene covalently linked to a porphyrin or related cyclic tetrapyrrole. The diagnostic agents preferentially localize in tumor tissue and fluoresce upon exposure to light. An improved method of synthesizing the diagnostic agents employed herein is also provided.

2. Prior Art

Carotenoid pigments, ubiquitous in photosynthetic membranes, are essential for the survival of green plants. Two facets of carotenoid function are recognized in photosynthetic membranes. First, carotenoids photoprotect by rapidly quenching chlorophyll triplet states which are formed in antenna systems or photosynthetic reaction centers. This triplet-triplet energy transfer prevents chlorophyll-photosensitized formation of highly destructive singlet oxygen which is injurious to the organism. In addition, carotenoids act as antennas by absorbing light in spectral regions where chlorophyll absorbs weakly and delivering the resulting exitation to chlorophyll via a singlet-singlet energy transfer process. Finally, nearby carotenoids quench chlorophyll first excited singlet states. This quenching has been ascribed to energy transfer or electron transfer or some other process leading to internal conversion and is believed to play a role in the regulation of photosynthesis.

A number of porphyrin materials have been found to localize in tumor tissue and to damage that tissue upon irradiation with light. Many of these are being investigated as therapeutic agents ("hematoporphyrin derivative" and related materials). All of these agents suffer from the problem that they are also absorbed by healthy tissue which is also harmed by the light.

Various synthetic carotenoids designed to mimic carotenoid photoprotection have been investigated by researchers at Arizona State University. Synthetic carotenoporphyrins consisting of a carotenoid part covalently linked to a synthetic meso-tetraarylporphyrin which successfully exhibited both the photophysical functions of cartenoids in photosynthesis were first reported by Gary Dirks, Ana L. Moore, Thomas A. Moore and Devens Gust in *Photochemistry and Photobiology*, Vol. 32, pp 277-280 (Permagon Press Ltd. Great Britain, 1980).

A carotenoporphyrin which demonstrated quenching of the porphyrin triplet state by the attached carotenoid via triplet-triplet energy transfer was reported by R. V. Bensasson, E. J. Land, A. L. Moore, R. L. Crouch, G. Dirks, T. A. Moore and D. Gust in *Nature*, Vol. 290, No. 5804, pp 329-332, Mar. 16, 1981.

Since that time, various compounds which exhibit the triplet-triplet energy transfer described in *Nature*, supra, have been reported by the Arizona State University group.

In 1984, carotenoporphyrins 1-5 were prepared by Dr. Paul Liddell at Arizona State University and reported in his doctoral thesis dated December, 1985. Carotenoporphyrins 1-3 were reported by Harry A. Frank, Barry W. Chadwick, Jung Jin Oh, Devens Gust et al., *Biochemical et Biophysical Acta* 892 (1987) 253-263.

It has now been discovered that certain synthetic carotenoporphyrins preferentially localize in mammalian tumor tissue where they absorb and emit light when irradiated with light so that the site of the tumor may be detected by the fluorescence of the localized carotenoporphyrin. Localization of the carotenoporphyrins employed in the practice of the present invention is better than that of porphyrins alone and most importantly, photodamage of tissue is precluded by the quenching of the porphyrin triplet state. Thus the present invention overcomes the problem inherent with the existing porphyrin photosensitizing compounds as diagnostic agents, that of collateral tissue damage. In fact, with the prior art porphyrins, the entire body of the mammalian host becomes photosensitive, and exposure of any body parts to light must be avoided for from several weeks to months after treatment.

SUMMARY OF THE INVENTION

The present invention provides a method of locating and visualizing mammalian tumor tissue comprising administering a diagnostically effective amount of a carotenoporphyrin 1-5 represented by the formula:

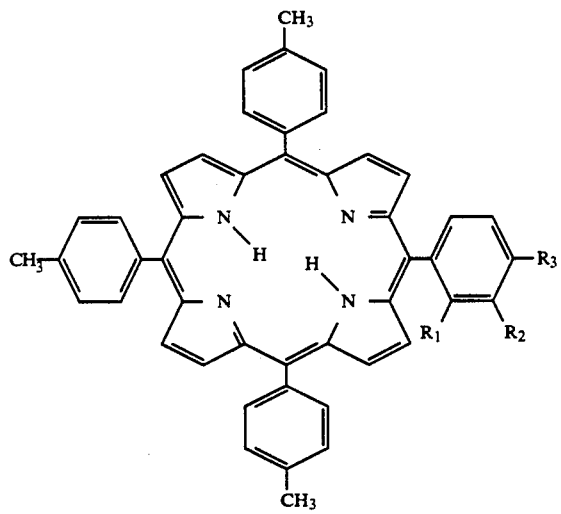

1: $R_1=R_2=H$, $R_3 =$

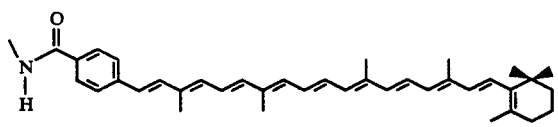

2: $R_1=R_3=H$, $R_2 =$

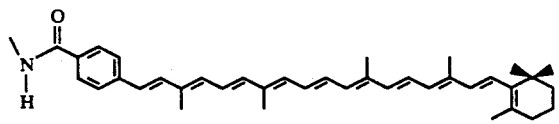

3: $R_2=R_3=H$, $R_1 =$

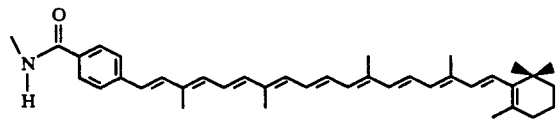

4: $R_1=R_2=H$, $R_3 =$

-continued

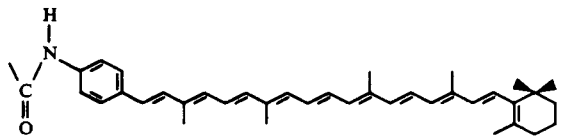

5: $R_2=R_3=H, R_1 =$

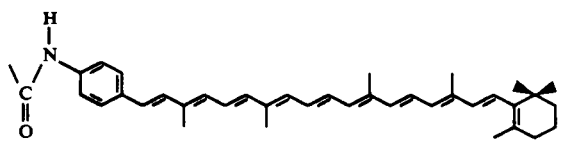

to a mammalian host, permitting the diagnostic agent to localize in the tumor tissue and thereafter irradiating the mammalian host with light whereby the localized carotenoporphyrin fluoresces sharply defining the tumor. Light emitted from the tumor by fluorescence of the localized diagnostic agent employed in this invention sharply defines the location of the tumor to be removed or otherwise treated.

Generally speaking, the diagnostic agents of the present invention were effectively administered to representative mammals in dosages of from 0.5 to 50 mg/kg of host body weight, preferably from 3 to 48 hours prior to the diagnostic procedure or surgery.

The diagnostic agents employed in the practice of the present invention have a number of advantages over current contrast agents and tumor diagnostic procedures. Their primary advantage is a lack of toxicity. Many individuals are sensitive to present contrast agents employed, for example in computer assisted tomography (CAT) scans and there have been cases of severe allergy reactions resulting in anaphylactic shock. For these sensitive individuals, nuclear scans are often employed. However, nuclear scans require the administration of radioactive diagnostic materials and further, are useful primarily to define function as opposed to structure. Magnetic resonance imaging does not require the use of a contrast diagnostic agent and while accurate and definitive for the diagnosis of brain and other abnormalities, is expensive, unpleasantly noisy, confining for claustrophobic individuals, and wholly unsuitable for use as an adjunct to surgery where it is desirable for the surgeon to be able to concurrently pinpoint the exact tumor location and follow his progress in excising it without damaging surrounding tissue or organs. Lower cost is an additional advantage of the present method.

The present invention also provides an improved, more convenient and economical synthesis of the diagnostic agents employed herein. Generally speaking, the porphyrin moieties were prepared by condensation of pyrrole and an appropriate mixture of aromatic aldehydes in propionic acid. The requisite carotenoid polyenes were prepared from 8'-apo-$\beta$-carotenal by means of a Wittig reaction and linked to the porphyrin via an acid chloride.

DETAILED DESCRIPTION OF PREFERRED EMBODIMENTS

In the examples reported below, the $^1$H NMR spectra were obtained at 300 to 500 MHz and used $\leq 1\%$ solutions in chloroform-d with tetramethylsilane as an internal reference. The UV-vis spectra were recorded on a HEWLETT PACKARD 8450A spectrophotometer.

For transient absorption studies, samples were placed in 1 cm$\times$1 cm$\times$4 cm cuvettes and deoxygenated by bubbling with argon. The apparatus used for the transient absorption work features excitation with ca. 15 ns pulses of less than 1 mJ at 590 nm. An adequate signal-to-noise ratio was achieved by signal averaging (typically about 500 flashes). The details of the spectrometer are described by Gust et al. *J. Am. Chem. Soc.* 1986, 108, 8028, incorporated by reference herein. Fluorescence decay measurements were made on ca. $1\times10^{-5}$M solutions using the time-correlated single photon counting method. The excitation source was a frequency-doubled, mode-locked Nd-YAG laser coupled to a synchronously pumped, cavity dumped dye laser with excitation at 590 nm. Detection was via a microchannel plate photomultiplier (Hamamatsu R2809U-01), and the instrument response time was ca. 35 ps.

In one embodiment of this invention, a method of administering a carotenoporphyrin that will preferentially localize in tumor tissue and absorb and emit light without damaging the mammalian host upon irradiation with light comprises the steps of administering a diagnostically effective amount of a carotenoporphyrin represented by the formula:

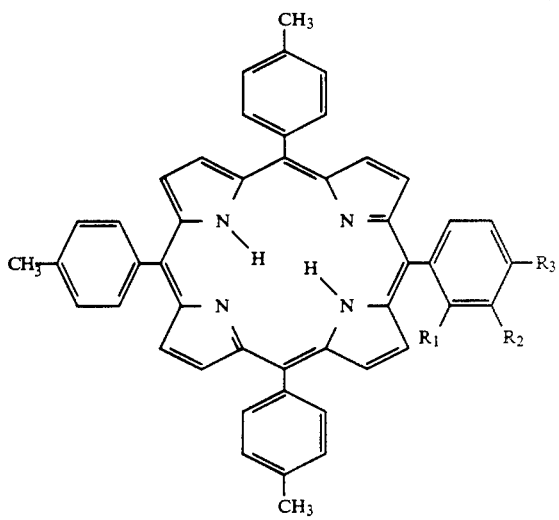

1: $R_1=R_2=H, R_3 =$

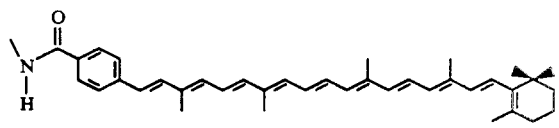

2: $R_1=R_3=H, R_2 =$

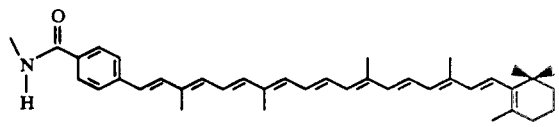

3: $R_2=R_3=H, R_1 =$

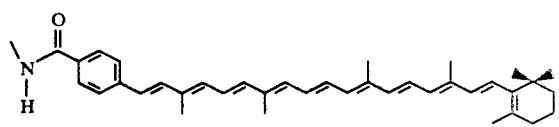

4: $R_1=R_2=H, R_3 =$

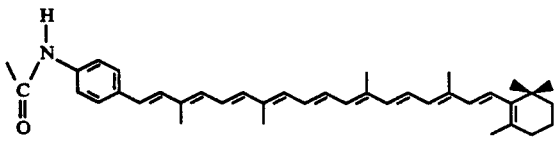

5: $R_2=R_3=H$, $R_1 =$

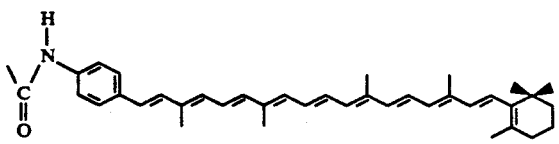

allowing said carotenoporphyrin to circulate and accumulate and localize in tumor tissue, preferably from about 3 to 48 hours prior to the diagnostic or surgical procedure, and exposing the mammalian host to light whereby said carotenoporphyrin fluoresces thereby permitting visualization and definition of the tumor tissue to be removed or treated.

More specifically, the carotenoporphyrin diagnostic agent employed in the practice of this invention localizes in tumor tissue, absorbs light of one wavelength, emits light of another wavelength by porphyrin fluorescence but does not damage healthy tissue. The process of this invention may be used both for diagnosis and as a valuable adjunct to surgery as light emitted from the tumor by fluorescence of the localized porphyrin in the carotenoporphyrin would sharply define the location of the tumor tissue to be removed.

In practice, a carotenoporphyrin of Formula I is administered intravenously to a mammalian host in a dosage of from 0.50 to 50 mg/kg (0.42 to 42 $\mu$mol/kg) of body weight from 3 to 48 hours prior to exposure to radiation having a wavelength of from about 300 to about 650 nanometers. The carotenoporphyrins may be conveniently administered either solubilized in an emulsion such as a CREMOPHOR EL emulsion (Sigma Chemical Company) or other suitable fatty emulsion or incorporated into liposomes such as unilamellar liposomes of a synthetic lipid such as dipalmitoylphosphatidylcholine ("DPPC") sold by Sigma Chemical Company, Inc. After the photosensitive diagnostic agent has had sufficient time to circulate and localize in tumor tissue, the mammalian host is exposed to a light whereby the carotenoporphyrin localized in tumor tissue fluoresces permitting visualization of the tumor location, size and configuration. Suitable light sources are those that emit radiation at wavelengths of between 300 to about 650 nanometers. The porphyrins have their strongest absorption bands at about 420, 518, 550 and 650 nanometers. Thus monochromatic radiation at these wavelengths would be preferentially absorbed. In addition to using the human eye as a detector, a light-sensitive electronic device such as a photomultiplier or photodiode array could be used as a detector to provide a picture or electronic image of localized material.

The present invention is quite suitable for visualization of mammalian tumors but may require additional work for effectual visualization of hepatic or splenic tumors because of the observed propensity of the selected carotenoporphyrins to localize in the liver and spleen of the host and thereby mask the results.

To further assist in the understanding of the present invention and not by way of limitation, the following examples are presented.

EXAMPLE 1

5-(-3-Aminophenyl)-10,15,20-tris(4-methylphenyl)porphyrin

To a 1-L flask equipped with a mechanical stirrer, condenser, and an addition funnel were added 300 mL of propionic acid, 22.54 g (0.188 mol) of p-tolualdehyde, and 11.3 g (0.075 mol) of m-nitrobenzaldehyde. The pale yellow solution was brought to reflux, and 16.77 g (0.25 mol) of pyrrole was added as rapidly as possible, without causing any overheating. Refluxing was continued for an additional 40 min. After cooling, the mixture was filtered, and the solid porphyrin mixture was washed with cold methanol until the filtrate was free of brown tar. After the remaining solid was dried, it (5.0 g) was dissolved in 150 mL of concentrated hydrochloric acid to which was added 10 g of stannous chloride dihydrate. The resulting green suspension was allowed to react for 40 min at 70° C., cooled, and treated with concentrated aqueous ammonia until a pH of 8 was obtained. The solution was then extracted several times with chloroform, and the combined organic extracts were washed with three 300-mL portions of 10% aqueous ammonia and then two 400-mL portions of water. The solution containing the mixture of aminoporphyrins was dried over sodium sulfate. In order to simplify the purification process, the mixture of porphyrins was converted to the N-acetyl form. The mixture was first dissolved in a solution of 400 mL of chloroform, 30 mL of pyridine, and 20 mL of acetic anhydride and allowed to stir at room temperature under a nitrogen atmosphere for 7 h. The solvent was then evaporated at reduced pressure, and residual pyridine and acetic anhydride were removed by azeotropic distillation with a 200-mL portion of toluene. The residue was dissolved in chloroform and washed with aqueous citric acid and aqueous sodium bicarbonate, and the solution was dried with sodium sulfate. Evaporation of the solvent at reduced pressure gave a purple solid, which was purified by column chromatography (silica gel/chloroform containing up to 2% acetone). The desired N-acetylporphyrin was collected, dissolved in chloroform, and refluxed for 30 min with 0.8 g of 2,3-dichloro-5,6-dicyanobenzoquinone to remove chlorins. After cooling, the solution was passed through a short bed of alumina to remove excess and reduced quinone. The eluate was evaporated to dryness at reduced pressure, and the residue was treated with 250 mL of concentrated hydrochloric acid for 19 h at 80° C. to hydrolyze the amide functionality. The green reaction mixture was cooled and neutralized with aqueous sodium hydroxide, and the reddish product was extracted with dichloromethane and recrystallized from dichloromethane/methanol to give 1.18 g of the desired porphyrin (2.8% yield): $^1$H NMR (300 MHz, CDCl$_3$) $\delta$-2.78 (2 H, s, pyrrole NH), 2.69 (9H, s, tolyl CH$_3$), 7.04–7.63 (4 H, m, 5 ArH), 7.54 (6 H, d, J=8.0 Hz, 10,15,20 ArH), 8.09 (6 H, d, J=8.0 Hz, 10,15,20 ArH), 8.85–8.94 (8 H, m, pyrrole H); mass spectrum (EI) m/z 671 (M+); UV-vis (dichloromethane)$\lambda_{max}$ (nm) 420, 518, 552, 592, 648.

EXAMPLE 2

5-(2-Aminophenyl)-10,15,20-tris(4-methylphenyl)porphyrin

The title compound was prepared using the method of Example 1 to give a 1.6% yield of the desired porphyrin: $^1$H NMR (300 MHz, CDCl$_3$) δ-2.74 (2 H, s, pyrrole NH), 2.70 (9H, s, tolyl CH$_3$), 7.09–7.90 (5 H, m, 5 ArH), 7.55 (6 H, d, J=7.8 Hz, 10,15,20 ArH), 8.09 (6 H, d, J=7.8 Hz, 10,15,20 ArH), 8.09 (6H, d, J=7.8 Hz, 10,15,20 ArH), 8.86–8.88 (8 H, m, pyrrole H); mass spectrum (EI) m/z 671 (M+); UV-vis (dichloromethane)$\lambda_{max}$ (nm) 418, 516, 552, 592, 648.

EXAMPLE 3

7'-Apo-7'-(4-carboxyphenyl)-β-carotene

Into a 200-mL flask outfitted with a magnetic stirring bar, a condenser and a gas inlet tube were placed 1.0 g (2.4 mmol) of 8'-apo-β-carotenal (Hoffman LaRoche), 50 mL of dimethyl sulfoxide, 1.4 g (2.9 mmol) of 4-carboxymethoxy- benzyltriphenylphosphonium bromide and 0.17 g (3.1 mmol) of sodium methoxide. The suspension was heated to 80° and stirred under an argon atmosphere. After 16 hr, supplemental amounts of both reactants were added and the reaction mixture was stirred for an additional 16 h. The reaction mixture was then poured into ether (800 ml) and the organic solution was washed six times with 150-mL portions of water to remove all traces of dimethyl sulfoxide. The ether layer was dried over anhydrous magnesium sulfate, the solvent was evaporated and the residue was recrystallized from methylene chloride-methanol to afford 1.12 g (85% yield) 7'-apo-7'-(4-carbomethoxyphenyl)-β-carotene: $^1$H NMR (90 MHzCDCl$_3$) δ1.03(6H,s,C16,C17), 1.10–1.80 (6H,m,C2,C3,C4), 1.72(3H,s,C18), 1.98(9H,s,C19,C20,C20'), 2.06(3H,s,C19'),6.1–7.0(14H,m,Vinyl-H), 7.05 and 8.05(4H,AB quartet,J=8.3Hz,Ar-H); mass spectrum (EI) m/z 549 (M+); UV-vis (toluene)$\lambda_{max}$ (nm) 302, 376, 458, 482, 514.

A 110 mg (0.2 mmol) sample of 7'-apo-7'-(4-carbomethoxyphenyl)-β-carotene was dissolved in tetrahydrofuran-methanol (3:1) (16 mL). To this solution was added 2 mL of 10% aqueous potassium hydroxide and the mixture was stirred under an argon atmosphere for 18 h. The above solution was then partitioned between chloroform and water (pH 1–2) and the aqueous layer washed with chloroform until all the carotene had been extracted. The combined chloroform extracts were dried over anhydrous sodium sulfate and filtered, and the solvent was evaporated to yield 98 mg (91%) of the title compound: $^1$H NMR (90 MHz CDCl$_3$)δ1.03(6H,s,C16,C17), 1.4–2.1(6H,m,C2,C3,C4), 1.72(3H,s,C18), 1.99(9H,s,C19,C20,C20'), 2.06(3H,s,C19'), 6.0–7.0(14H, m, vinyl-H), 7.4–8.1(4-H,AB quartet,Ar-H); mass spectrum (EI) m/z 535 (M+)$\lambda_{max}$ (nm) (methylene chloride), 302,376,458,482,514.

EXAMPLE 4

Carotenoporphyrin 1

To a 50-mL flask were added 70 mg (0.01 mmol) of 7'-apo-7'-(4-carboxyphenyl)-β-carotene (Example 3), 20 mL of dry benzene, 29 μL (0.40 mmol) of thionyl chloride, and 80 μL (0.99 mmol) of dry pyridine. The initial orange suspension was rapidly converted into the acid chloride as indicated by a dark red color. After the solution was stirred for 30 min under argon, the solvent was distilled under vacuum. Benzene (40 mL) was added and evaporated to dryness under vacuum to remove excess thionyl chloride. The residue that remained was dissolved in 30 mL of dry dichloromethane and added to a solution of 133 mg (0.198 mmol) of 5-(4-aminophenyl)-10,15,20-tris(4-methylphenyl)porphyrin which was dissolved in 60 mL of dry dichloromethane and 0.2 mL of dry pyridine. This solution was stirred under argon for 60 min and then partitioned between dichloromethane and water. The organic layer was washed twice with 70-mL portions of water, the solvent was evaporated, and the residue was dried under vacuum. Chromatography on silica gel with toluene/0.5% ethyl acetate as the solvent and subsequent recrystallization from methylene chloride/methanol gave 82 mg (53% yield) of the carotenoporphyrin 1: $^1$H NMR (400 MHz, CDCl$_3$) δ1.05 (6 H, s, C16,C17), 1.48 (2 H, m, C2), 1.62 (2 H, m, C3), 1.73 (3 H, s, C18), 1.99–2.04 (11 H, m, C19, C20, C20',C4), 2.09 (3 H, s, C19', 2.71 (9 H, s, tolyl CH$_3$), 6.0–7.1, (14 H, m, vinyl H), 7.55 (6 H, d, J=5.9 Hz, 10,15,20Ar3,5H), 7.61 (2 H, d, J=6.4 Hz, C2', C4'), 7.98 (2 H, d, J=6.4 Hz, C1',C5'), 8.03 (2 H, d, J=6.6 Hz, 5Ar3,5H), 8.06 (6 H, d, J=6.1 Hz, 10,15,20Ar2,6H), 8.15 (1 H, s, NH), 8.22 (2 H, d, J =6.6 Hz, 5Ar2,6H), 8.87 (8 H, m, pyrrole H); UV-vis (dichloromethane)$\lambda_{max}$ (nm) 376, 418, 480, 512, 550 (sh), 590, 648.

EXAMPLE 5

Carotenoporphyrin 2

Carotenoporphyrin 2 was prepared following the method of Example 4 using 133 mg (0.198 mmol) 5-(3-aminophenyl)-10,15,20-tris(4-methylphenyl)porphyrin to give 79 mg (51%) of product: $^1$H NMR (500 MHz, CDCl$_3$) δ1.04 (6 H, m, C16,C17), 1.48 (2 H, m, C2), 1.63 (2 H, m, C3), 1.73 (3 H, s, C18), 1.98 (9 H, s, C19,C20,C20'), 2.02 (3 H, s, C19'), 2.70–2.71 (9 H, m, tolyl CH$_3$), 6.0–7.0 (14 H, m, vinyl H), 7.44 and 7.83 (4 H, AB, C1',C5',C2',C4'), 7.55 (6 H, m, 10,15,20Ar3,5H), 8.85 (8 H, m, pyrrole H); UV-vis (dichloromethane)$\lambda_{max}$ (nm) 373, 418, 480, 512, 550 (sh), 590, 646.

EXAMPLE 6

Carotenoporphyrin 3

Carotenoporphyrin 3 was prepared following the procedure of Example 4 using 133 mg (0.198 mmol) of 5-(2-aminophenyl)-10,15,20-tris(4-methylphenyl)porphyrin to yield 49 mg (32%) of the desired product: $^1$H NMR (500 MHz, CDCl$_3$) δ1.03–1.06 (6 H, m, C16,C17), 1.48 (2 H, m, C2), 1.62 (2 H, m, C3), 1.72 (3 H, s, C18), 1.87 (3 H, s, C19'), 1.96–1.98 (9 H, s, C19,C20,C20'), 2.0 (2 H, m, C4), 2.70–2.72 (9 H, m, tolyl CH$_3$), 5.90–6.90 (14 H, m, vinyl H), 6.43 and 6.49 (4H, AB, J=8.5 Hz, ArH), 7.50–8.20 (12 H, m, ArH), 8.80–9.10 (8 H, m, pyrrole H); UV-vis (dichloromethane)$\lambda_{max}$ (nm) 373, 418, 480, 550 (sh), 590, 648.

EXAMPLE 7

7'-Apo-7'-(4-aminophenyl)-β-carotene

To a 100-mL flask were added 0.50 g (1.2 mmol) of 8'-apo-β-carotenal, 80 mL of dimethyl sulfoxide, 1.1 g (2.4 mmol) of [4-(N-acetylamino)benzyl]triphenylphosphonium bromide and 0.20 g (3.7 mmol) of sodium methoxide. The mixture was stirred for 5 h under argon at 60°–70° C. and was then quenched by pouring the dark orange solution into 500 mL of ether and washing the resulting solution with water repeatedly in order to remove most of the dimethyl sulfoxide. The organic layer was dried over anhydrous magnesium sulfate and filtered, and the solvent was evaporated under reduced pressure. The resulting crude carotenoid amide was dissolved in 30 mL of tetrahydrofuran to which 75 mL of saturated methanolic potassium hydroxide solution was added. This solution was heated to 63° C., stirred under an argon atmosphere for 5.5 h, and then poured into 500 mL of ether and washed six times with 150-mL portions of water. The organic layer was dried over anhydrous magnesium sulfate and filtered, and the solvent was evaporated. The residue was chromatographed with chloroform on a dry-packed silica gel column to give 319 mg (53% yield) of the pure aminocarotenoid: $^1$H NMR (400 MHz, CDCl$_3$)$\delta$1.03 (6 H, s, C16,C17), 1.48 (2 H, m, C2), 1.61 (2 H, m, C3), 1.72 (3 H, s, C18), 1.97-1.98 (9 H, m, C19,C20,C20'), 2.0 (2 H, m, C4), 2.02 (3 H, s, C18'), 3.75 (2 H, s, NH$_2$), 6.11-6.76 (14H, m vinyl H), 7.25-7.28 (4 H, m, ArH); mass spectrum (EI) m/z 506 (M+); UV-vis (dichloromethane)$\lambda_{max}$ (nm) 376, 478, 506.

EXAMPLE 8

Carotenoporphyrin 4

To a 50-mL flask equipped with a condenser and nitrogen gas line were added 120 mg (0.17 mmol) of 5-(4-carboxyphenyl)-10,15,20-tris(4-methylphenyl)porphyrin (J. A. Anton et al., *J. Heterocyclic Chem.* 1976, 13, 717), 30 mL of dichloromethane, and 3.0 mL of oxalyl chloride. The dark green solution was refluxed under nitrogen for 1 h and cooled, and the solvent was evaporated under vacuum. Two 25-mL portions of toluene were successively added and then evaporated under vacuum in order to remove all traces of excess oxalyl chloride. The residue was dissolved in a mixture of dichloromethane (50 mL) and pyridine (1 mL). The resulting solution was added to 70 mg (0.138 mmol) of 7'-apo-7'-(4-aminophenyl)-$\beta$-carotene dissolved in 50 mL of dichloromethane and stirred under argon. After 1 h, the reaction mixture was poured into 180 mL of dichloromethane and washed twice with 100-mL portions of water. The organic layer was separated, and the solvent evaporated. Residual water and pyridine were removed by azeotropic distillation with toluene. The residue was chromatographed on silica gel (dichloromethane), and the product was recrystallized from dichloromethane/methanol to afford 76 mg (46% yield) of the pure carotenoporphyrin 4: $^1$H NMR (400 MHz, CDCl$_3$) $\delta$1.03 (6 H, m, C16,C17), 1.47 (2 H, m, C2), 1.62 (2 H, m, C3), 1.72 (3 H, s, C18), 1.98-2.01 (9 H, m, C19,C20,C20'), 2.02-2.06 (2 H, m, C4'), 2.08 (3 H, s, C19'), 2.71 (9 H, s, tolyl CH$_3$), 6.0-7.0 (14 H, m, vinyl H), 7.52-7.60 (8 H, m, 10,15,20Ar3,5H and C2',C4'), 7.77 (2 H, d, J=8.6 Hz, C1',C5'), 8.10 (6 H, d, J=7.9 Hz, 10,15,20Ar2,6H), 8.14 (1 H, s, NH), 8.26 and 8.35 (4 H, AB, J =8.2 Hz, 5ArH), 8.78-9.00 (8 H, m, pyrrole H); UV-vis (dichloromethane)$\lambda_{max}$ (nm) 373, 418, 476, 510, 550 (sh), 592, 648.

EXAMPLE 9

Carotenoporphyrin 5

Carotenoporphyrin 5 was prepared following the method of Example 8 from 100 mg (0.143 mmol) of 5-(2-carboxyphenyl)-10,15,20-tris(4-methylphenyl)porphyrin. (J. A. Anton et al., *J. Heterocyclic Chem.* 1975, 12. 573. A total of 77 mg of pure product was obtained (45% yield): $^1$H NMR (400 MHz, CDCl$_3$)$\delta$1.02-1.05 (6 H, m, C16,C17), 1.47 (2 H, m, C2), 1.60 (2 H, m, C3), 1.69 (3 H, s, C18), 1.71 (3 H, s, C19') 1.86 (3 H, s, C20'), 1.95-1.97 (6 H, m, C19,C20,), 2.01-2.05 (2 H, m, C4), 2.70 (9 H, s, tolyl CH$_3$), 5.50-6.80 (14 H, m, vinyl H), 7.03 (1 H, s, NH), 7.50-8.50 (20 H, m, Ar H), 8.77-8.91 (8 H, m, pyrrole H); UV-vis (dichloromethane)$\lambda_{max}$ (nm) 372, 418, 478, 512, 550 (sh), 592, 648.

EXAMPLE 10

Porphyrin 6

To a 100-mL flask were added 110 mg (0.16 mmol) of 5-(4-aminophenyl)-10,15,20,tris(4-methylphenyl)porphyrin, 40 mL of dichloromethane, and 40 $\mu$L (0.49 mmol) of pyridine. The mixture was stirred under a nitrogen atmosphere and 37 $\mu$L (0.32 mmol) of benzoyl chloride was added. The reaction was complete after 30 min. The mixture was diluted with 60 mL of dichloromethane and washed with dilute hydrochloric acid, aqueous sodium bicarbonate and aqueous sodium chloride. The resulting organic phase was dried over anhydrous sodium sulfate and filtered, and the solvent was distilled from the filtrate under reduced pressure. The resulting purple solid was recrystallized from dichloromethane/methanol to give 115 mg (92% yield) of the desired porphyrin: $^1$H NMR (300 MHz, CDCl$_3$) $\delta$-2.77 (2 H, s, pyrrole NH), 2.71 (9 H, s, tolyl CH$_3$), 7.56 (6 H, d, J=7.9 Hz, 10,15,20ArH), 7.60-8.07 (5 H, m, ArH), 8.05 (2 H, d, J=8.3 Hz, 5ArH), 8.10 (6 H, d, J=7.9 Hz, 10,15,20ArH), 8.16 (1 H, s, NH), 8.24 (2 H, d, J=8.3 Hz, 5ArH), 8.87-8.88 (8 H, m, pyrrole H); mass spectrum (EI) m/z 775 (M+); UV-vis (dichloromethane)$\lambda_{max}$ (nm) 420, 518, 554, 594, 650.

EXAMPLE 11

In vivo uptake of carotenoporphyrin 1

Carotenoporphyrin 1 (5 mg/kg, 4.2 $\mu$mol/kg body weight) solubilized in CREMOPHOR EL (castor oil and ethylene oxide) emulsion (Sigma Chemical Company, Inc.) was injected into Balb/c mice bearing a transplanted MS-2 fibrosarcoma. Carotenoporphyrin levels in serum and selected organs and tissues were measured 3, 24, 48 and 96 hours following injection by absorption and fluorescence. Carotenoporphyrin levels are set forth in Table I.

TABLE 1

| | Carotenoporphyrin Levels ($\mu$g/g) | | | | | | |
|---|---|---|---|---|---|---|---|
| Mouse | Serum | Tumor | Liver | Spleen | Muscle | Skin | Time |
| 1 | 28.97 | 2.69 | 7.65 | 4.01 | 0.26 | 0.43 | |
| 2 | 32.33 | 2.45 | 7.29 | 3.74 | 0.30 | 0.34 | |
| 3 | 26.38 | 3.32 | 7.98 | 4.24 | 0.25 | 0.32 | 3 h |
| average | 29.23 | 2.82 | 7.64 | 4.00 | 0.27 | 0.36 | |
| s.d | 2.98 | 0.45 | 0.35 | 0.25 | 0.03 | 0.06 | |
| 4 | 1.3 | 4.84 | 22.19 | 11.35 | 0.24 | 0.63 | |
| 5 | 0.93 | 5.82 | 24.77 | 10.76 | 0.39 | 0.84 | |
| 6 | 1.23 | 7.85 | 24.77 | 11.66 | 0.41 | 0.62 | 24 h |
| average | 1.18 | 6.17 | 27.48 | 11.16 | 0.35 | 0.70 | |
| s.d. | 0.23 | 1.54 | 7.04 | 0.62 | 0.09 | 0.12 | |
| 7 | 0.12 | 5.62 | 30.42 | 15.75 | 0.39 | 0.92 | |
| 8 | 0.13 | 5.11 | 25.27 | 9.94 | 0.33 | 0.66 | |
| 9 | 0.16 | 6.51 | 30.16 | 14.09 | 0.44 | 0.82 | 48 h |
| average | 0.14 | 5.75 | 28.62 | 13.26 | 0.39 | 0.80 | |
| s.d | 0.02 | 0.71 | 2.90 | 2.99 | 0.06 | 0.13 | |
| 10 | 0.03 | 2.57 | 25.80 | 10.34 | 0.27 | 0.68 | |
| 11 | 0.02 | 3.07 | 26.16 | 11.37 | 0.30 | 0.70 | |
| 12 | 0.02 | 2.58 | 26.04 | 7.33 | 0.29 | 0.48 | 96 h |
| average | 0.03 | 2.74 | 26.00 | 9.68 | 0.29 | 0.62 | |
| s.d | 0.002 | 0.29 | 0.18 | 2.10 | 0.02 | 0.12 | |

EXAMPLE 12

The procedure of Example 11 was repeated using 9.86 mg/kg (8.4 μmoles/kg) of body weight of the diagnostic material of Example 12. The results are summarized in Table II.

TABLE II

| Mouse | Carotenoporphyrin Levels (μg/g) | | | | | | Time |
|---|---|---|---|---|---|---|---|
|  | Serum | Tumor | Liver | Spleen | Muscle | Skin |  |
| 1 | 66.20 | 7.66 | 15.34 | 3.95 | 0.91 | 0.88 |  |
| 2 | 60.00 | 6.88 | 14.82 | 3.13 | 1.44 | 1.15 |  |
| 3 | 52.76 | 8.36 | 15.69 | 3.00 | 1.13 | 1.07 | 3 h |
| average | 59.65 | 7.63 | 15.28 | 3.36 | 1.16 | 1.03 |  |
| s.d | 6.73 | 0.74 | 0.44 | 0.51 | 0.27 | 0.14 |  |
| 4 | 3.05 | 12.65 | 43.59 | 9.61 | 1.02 | 1.54 |  |
| 5 | 4.63 | 14.80 | 51.03 | 12.62 | 0.95 | 1.13 |  |
| 6 | 4.32 | 17.40 | 53.65 | 15.63 | 1.53 | 1.98 | 24 h |
| average | 4.00 | 14.95 | 49.42 | 12.62 | 1.16 | 1.55 |  |
| s.d. | 0.84 | 2.38 | 5.22 | 3.01 | 0.32 | 0.42 |  |

EXAMPLE 13

The procedure of Example 11 was repeated using 1 mg/kg (0.84 μmoles/kg) of body weight of the carotenoporphyrin incorporated into unilamellar liposomes of DPPC (dipalmitoylphosphatidylcholine, Sigma Chemical Company). The results are set forth in Table III.

TABLE III

| Mouse | Carotenoporphyrin Levels (μg/g) | | | | | | Time |
|---|---|---|---|---|---|---|---|
|  | Serum | Tumor | Liver | Spleen | Muscle | Skin |  |
| 1 | 0.20 | 0.34 | 9.66 | 9.82 | 0.09 | 0 |  |
| 2 | 0.21 | 0.47 | 10.53 | 9.17 | 0.22 | 0 |  |
| 3 | 0.16 | 0.37 | 9.43 | 8.20 | 0 | 0 | 3 h |
| average | 0.19 | 0.09 | 9.87 | 9.06 | 0.11 | 0 |  |
| s.d | 0.03 | 0.45 | 0.58 | 0.08 | 0.11 | 0 |  |
| 4 | 0.08 | *0.14 | 8.87 | 5.68 | 0.07 | 0 |  |
| 5 | 0.13 | 1.19 | 9.34 | 4.33 | 0 | 0 |  |
| 6 | 0.10 | 0.74 | 9.24 | 5.74 | 0.05 | 0 | 8 h |
| average | 0.10 | 0.97 | 9.15 | 5.25 | 0.04 | 0 |  |
| s.d. | 0.03 | 0.32 | 0.25 | 0.80 | 0.04 | 0 |  |
| 7 | 0.05 | 0.23 | 7.78 | 8.64 | 0.09 | 0.11 |  |
| 8 | 0.04 | 0.18 | 9.01 | *4.47 | 0 | 0.05 |  |
| 9 | 0.07 | 0.18 | 9.11 | 8.18 | 0 | 0 | 24 h |
| average | 0.05 | 0.20 | 8.63 | 8.41 | 0.03 | 0.05 |  |
| s.d | 0.02 | 0.03 | 0.74 | 0.33 | 0.05 | 0.06 |  |
| 10 | 0.01 | 0.19 | 6.77 | 6.09 | 0.31 | 0.05 |  |
| 11 | 0.02 | 0.28 | 7.94 | 6.08 | 0 | 0.09 |  |
| 12 | 0.01 | 0.18 | 7.73 | 4.82 | 0.14 | 0 | 48 h |
| average | 0.01 | 0.22 | 7.48 | 5.66 | 0.15 | 0.05 |  |
| s.d | 0.01 | 0.05 | 0.62 | 0.73 | 0.16 | 0.05 |  |

*Not considered in averaging data

EXAMPLE 14

The procedure of Example 13 was repeated using i.v. injections of 0.65 mg/kg (0.84 μmoles/kg) of body weight of the carotenoporphyrin incorporated into unilamellar liposomes of DPPC (dipalmitoylphosphatidylcholine, Sigma Chemical Company) The results are set forth in Table IV.

TABLE IV

| Mouse | Carotenoporphyrin Levels (μg/g) | | | | | | Time |
|---|---|---|---|---|---|---|---|
|  | Serum | Tumor | Liver | Spleen | Muscle | Skin |  |
| 1 | 0.18 | 0.11 | 11.00 | 2.43 | 0.11 | 0.02 |  |
| 2 | 0.19 | 0.13 | 7.10 | 2.12 | 0.09 | 0 |  |
| 3 | 0.10 | 0.05 | 2.37 | 1.25 | 0.09 | 0.05 | 3 h |
| average | 0.16 | 0.10 | 4.53 | 1.93 | 0.10 | 0.02 |  |
| s.d | 0.05 | 0.04 | 2.39 | 0.61 | 0.01 | 0.02 |  |
| 4 | 0.04 | 0.14 | 5.36 | 3.13 | 0.03 | 0.03 |  |
| 5 | 0.04 | 0.09 | 5.22 | 2.10 | 0.02 | 0.07 |  |
| 6 | 0.03 | 0.15 | 6.83 | 1.52 | 0.02 | 0.05 | 24 h |
| average | 0.04 | 0.13 | 5.80 | 2.25 | 0.02 | 0.05 |  |
| s.d. | 0.01 | 0.03 | 0.89 | 0.81 | 0.01 | 0.02 |  |

The mechanism of the carotenoporphyrins employed in the present invention generally works as follows. C-P represents a porphyrin (P) covalently attached to a carotenoid (C) by chemical bonds. In use, the following sequence occurs:

C-P is administered to a mammalian host and localizes in tumor tissue with small amounts deposited in other tissues and larger amounts deposited in the spleen and liver. The tissue is irradiated with light (hv) and some is absorbed by the porphyrin producing the porphyrin first excited single state, C-$^1$P, according to the following reaction sequence:

$$C\text{-}P + hv \rightarrow C\text{-}^1P$$

Some of the porphyrin singlet states emit light of a different wavelength (fluoresce)(hv') and this is detected by the surgeon or physician. This sequence is represented as follows:

$$C\text{-}^1P \rightarrow C\text{-}P + hv'$$

Some of the porphyrin singlet states undergo intersystem crossing to form the triplet state of the porphyrin, C-$^3$P as follows:

$$C\text{-}^1P \rightarrow C\text{-}^3P$$

Before the porphyrin triplet state can react with oxygen or other molecules to initiate tissue damage, the carotenoid quenches it by energy transfer:

$$C\text{-}^3P \rightarrow {}^3C\text{-}P$$

The carotenoid triplet state $^3$C-P is harmless and decays to the normal ground state C-P without doing any damage and is eventually excreted by the host organism.

From the foregoing, it is readily apparent that a useful embodiment of the present invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. A method of locating a diagnostic agent in and visualizing non-hepatic and non-splenic tumor tissue in a mammalian host comprising: administering to a mammalian host an effective amount of a carotenoporphyrin represented by the formula:

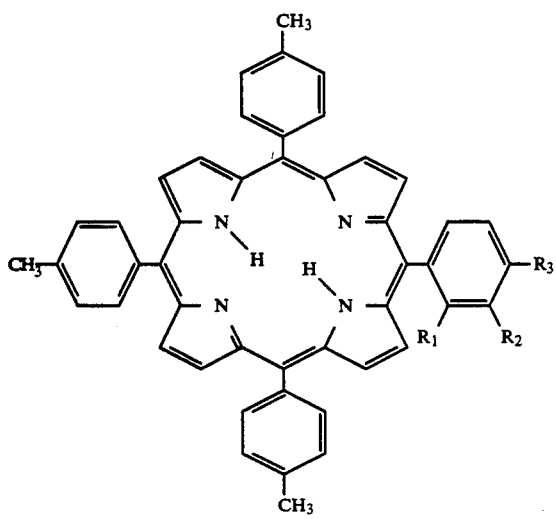

1: $R_1=R_2=H$, $R_3 =$

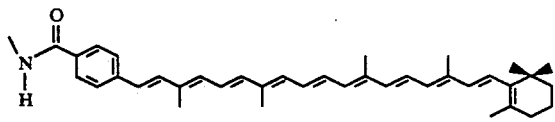

2: $R_1=R_3=H$, $R_2 =$

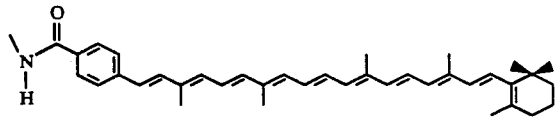

3: $R_2=R_3=H$, $R_1 =$

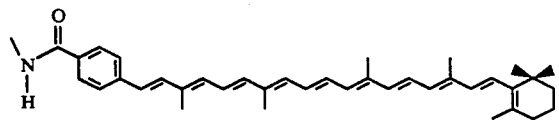

4: $R_1=R_2=H$, $R_3 =$

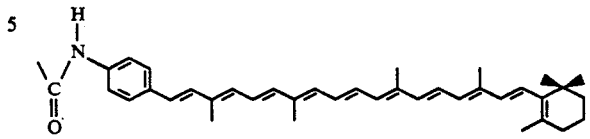

5: $R_2=R_3=H$, $R_1 =$

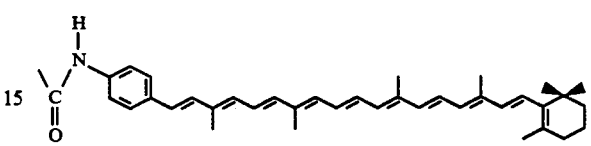

permitting said carotenoporphyrin to localize in the tumor tissue; and thereafter exposing said mammalian host to light whereby said carotenoporphyrin fluoresces permitting precise visualization of the tumor location, size and shape.

2. The method of claim 1 wherein said carotenoporphyrin is administered intravenously prior to initiation of a diagnostic or surgical procedure.

3. The method of claim 2 wherein said carotenoporphyrin is administered intravenously as a solubilized emulsion.

4. The method of claim 2 wherein said carotenoporphyrin is incorporated into liposomes prior to administration.

5. The method of claim 1 wherein said carotenoporphyrin is carotenoporphyrin 1.

6. The method of claim 1 wherein said carotenoporphyrin is carotenoporphyrin 2.

7. The method of claim 1 wherein said carotenoporphyrin is carotenoporphyrin 3.

8. The method of claim 1 wherein said carotenoporphyrin is carotenoporphyrin 4.

9. The method of claim 1 wherein said carotenoporphyrin is carotenoporphyrin 5.

* * * * *